United States Patent
George et al.

(10) Patent No.: US 8,052,594 B2
(45) Date of Patent: Nov. 8, 2011

(54) PROSTHETIC DEVICE WITH PROTRUSIONS FOR GIRTH

(75) Inventors: Stephanie A. George, St. Louis Park, MN (US); Charles C. Kuyava, Eden Prairie, MN (US); Sara E. Nelson, Plymouth, MN (US); Randall P. Rowland, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 329 days.

(21) Appl. No.: 12/274,675

(22) Filed: Nov. 20, 2008

(65) Prior Publication Data

US 2009/0131745 A1    May 21, 2009

Related U.S. Application Data

(60) Provisional application No. 60/989,373, filed on Nov. 20, 2007.

(51) Int. Cl.
*A61F 5/00* (2006.01)

(52) U.S. Cl. .......................................................... 600/40

(58) Field of Classification Search .............. 600/38–41; 623/14.13, 13.11, 11.11, 23.5, 13.19, 23.31, 623/16.11, 19.13, 19.14, 2, 0.15
See application file for complete search history.

(56) References Cited

U.S. PATENT DOCUMENTS

| | | |
|---|---|---|
| 3,832,996 A | 9/1974 | Kalnberz |
| 3,893,456 A | 7/1975 | Small et al. |
| 3,987,789 A | 10/1976 | Timm et al. |
| 3,991,752 A | 11/1976 | Gerow |
| 4,066,073 A | 1/1978 | Finney et al. |
| 4,151,840 A | 5/1979 | Barrington |
| 4,177,805 A * | 12/1979 | Tudoriu ........................ 600/40 |
| 4,187,839 A | 2/1980 | Nuwayser et al. |
| 4,204,530 A | 5/1980 | Finney |
| 4,244,370 A | 1/1981 | Furlow et al. |
| 4,345,339 A | 8/1982 | Muller et al. |
| 4,353,360 A | 10/1982 | Finney et al. |
| 4,392,562 A * | 7/1983 | Burton et al. .................. 600/40 |
| 4,411,260 A | 10/1983 | Koss |
| 4,411,261 A | 10/1983 | Finney |
| 4,483,331 A | 11/1984 | Trick |
| 4,517,967 A | 5/1985 | Timm et al. |
| 4,522,198 A | 6/1985 | Timm et al. |
| 4,541,420 A | 9/1985 | Timm et al. |
| 4,545,081 A | 10/1985 | Nestor et al. |
| 4,594,998 A | 6/1986 | Porter et al. |
| 4,619,251 A | 10/1986 | Helms et al. |

(Continued)

FOREIGN PATENT DOCUMENTS

| | | |
|---|---|---|
| EP | 0137752 B1 | 8/1989 |
| EP | 0774935 B1 | 7/1995 |
| GB | 2151484 A | 7/1985 |
| WO | WO8601398 A1 | 3/1986 |
| WO | WO9604865 A1 | 2/1996 |

OTHER PUBLICATIONS

Acu-Form Penile Prosthesis, Mentor, 1 page Aug. 1997.

(Continued)

*Primary Examiner* — Samuel Gilbert
(74) *Attorney, Agent, or Firm* — Westman, Champlin & Kelly, P.A.

(57) ABSTRACT

A prosthetic device comprises a column formed of resilient material. The column comprises external protrusions that vary a girth of the column. The protrusions are separated by valleys that reduce bulk.

16 Claims, 2 Drawing Sheets

U.S. PATENT DOCUMENTS

| | | | |
|---|---|---|---|
| 4,665,902 A | 5/1987 | Goff et al. | |
| 4,666,428 A * | 5/1987 | Mattioli et al. | 600/40 |
| 4,669,456 A | 6/1987 | Masters | |
| 4,693,719 A | 9/1987 | Franko et al. | |
| 4,699,128 A | 10/1987 | Hemmeter | |
| 4,807,608 A | 2/1989 | Levius | |
| 4,881,531 A | 11/1989 | Timm et al. | |
| 4,899,737 A | 2/1990 | Lazarian | |
| 4,988,357 A * | 1/1991 | Koss | 600/40 |
| 5,050,592 A * | 9/1991 | Olmedo | 600/40 |
| 5,176,708 A | 1/1993 | Frey et al. | |
| 5,263,436 A * | 11/1993 | Axelrod | 119/710 |
| 5,283,390 A | 2/1994 | Hubis et al. | |
| 5,445,594 A | 8/1995 | Elist | |
| 5,468,213 A * | 11/1995 | Polyak | 600/40 |
| 5,509,891 A | 4/1996 | DeRidder | |
| 5,512,033 A * | 4/1996 | Westrum et al. | 600/40 |
| 5,553,379 A | 9/1996 | Westrum, Jr. et al. | |
| 6,579,230 B2 | 6/2003 | Yachia et al. | |
| 6,600,108 B1 | 7/2003 | Mydur et al. | |
| 2005/0014993 A1 | 1/2005 | Mische | |
| 2008/0103353 A1 | 5/2008 | Jahns et al. | |
| 2009/0132044 A1 | 5/2009 | George et al. | |
| 2009/0216326 A1* | 8/2009 | Hirpara et al. | 623/13.14 |

OTHER PUBLICATIONS

Agrawal, Wineet, et al., An Audit of Implanted Penile Prostheses in The UK, BJU International pp. 393-395 (2006).

Akand, Murat Mechanical Failure With Malleable Penile Prosthesis, J. Urol. 70: 1007.e11-1007.e12 (2007).

AMS Malleable 600.TM. American Medical Systems Publication 30915, 1983.

Anafarta, Kadri, Clinical Experience With Inflatable and Malleable Penile Implants in 104 Patients, Urol. Int. 56: 100-104 (1996).

Benson RC Jr, Patterson DE, Barrett DM. Long-term results with the Jonas malleable penile prosthesis. J Urol. Nov. 1985;134(5):899-901.

Burns-Cox, N., Fifteen Years Experience of Penile Prosthesis Insertion, International J. Impotence Res. (1997) 9, 211-216.

Chiang, Han-Sun, 10 Years of Experience With Penile Prosthesis Implantation in Taiwanese Patients, J. Urol. vol. 163: 476-480 (2000).

Choi, Hyung Ki, Ten Years of Experience With Various Penile Prosthesis in Korean, Yasel Medical J. Wol. 35, No. 2, (1994) 209-217.

Dorfinger T, Bruskewitz R. AMS malleable penile prosthesis, Urology. Dec. 1986;28(6):480-5.

Durazi, Mohammed et al., Penile Prosthesis Implantation for Treatment of Postpriapism Erectile Dysfunction, Urol. J. 2008:5:115-9.

Fathey, Ahmad, Experience With Tube (Promedon_Malleable Penile Implant, Urol. Int. 2007; 79:244-247.

Ferguson, Kenneth, Prospective Long-Term Results and Quality-of-Life-Assessment After Dura-II Penile Prosthesis Placement, Urol. 61(2) 437-441 (2003).

Fogarty, JD, Cutaneous Temperature Measurements in Men With Penile Prostheses: A Comparison Study, Int. J. of Impotence Res. (2005) 17, 506-509.

Henry, Gerard D., Advances in Penile Prosthesis Design, Curr Sex Health report 2007;4:15-19.

Jonas U. [Silicone-silver penis prosthesis (Jonas-Eska), long-term reconstruction. J Urol. Sep. 1998;160(3 Pt 2):1164-8.

Kardar, A.H., An Unusual Complication of Penile Prosthesis Following Urethroplasty, Scand. J. Urol. Nephrol. 36: 89-90, 2002.

Kaufman JJ, Raz S. Use of implantable prostheses for the treatment of urinary incontinence and impotence. Am J Surg. Aug. 1975;130(2):244-50.

Khoudary, Kevin, Design Considerations in Penile Prostheses: The American Medical Systems Product Line, J. Long-Term Effects of Medical Implants, 7(1):55-64 (1997).

Kimoto, Yasusuke et al., JSSM Guidleines for Erectile Dysfunction, Int. J. Urol (2008) 15, 564-76.

Krauss, Dennis J., Use of The Malleable Penile Prosthesis in The Treatment of Erectile Dysfunction: A Prospective Study of Postoperative Adjustment, J. Urol. vol. 142: 988-991 (1989).

Lazarou, Stephen, Technical Advances in Penile Prostheses, J. Long-Term effects of Medical Implants, 16(3):235-247 (2006).

Leriche, Albert, et al., Long-Term Outcome of Forearm Flee-Flap Phalloplasty in The Treatment of Transexualism, BJU Int. (2008) 101, 1297-1300.

Maul Judd, Experience With The AMS 600 Malleable Penile Prosthesis, J Urol. 135:929-931 (1986).

Mentor Urology Products, 18 pages (May 1998).

Merino, G. Atienza, Penile Prosthesis for The Treatment of Erectile Dysfunction, Actas Urol. Esp. 2006: 30 (2): 159-169.

Minervini, Andrea, Outcome of Penile Prosthesis Implantation for Treating Erectile Dysfunction: Experience With 504 Procedures, BJU International 97:129-133, (2005).

Montague, Drogo, Clinical Guidelines Panel on Erectile Dysfunction: Summary Report on the Treatment of Organic Erectile Dysfunction, J. Urol. 156:2007-2011 (1996).

Montague, Drogo, Contemporary Aspects of Penile Prosthesis Implantation urol Int. 2003: 70: 141-146.

Montague, Drogo, Current Status of Penile Prosthesis Implantation, Urology Reports 2000, 1: 291-296.

Montague, Drogo, Experience With Semirigid Rod and Inflatable Penile Prostheses, J. Urol. 129:967-968, 1983.

Montague, Drogo, Penile Prosthesis Implantation for End-Stage Erectile Dysfunction After Radical Prostatectomy, Reviews in Urol. vol. 7 Suppl. 2 S51-S57 2005.

Montague, Drogo, Penile Prosthesis Implantation, 712-719 1994.

Montague, Drogo, Surgical Approaches for Penile Prostheses Implantation: Penoscrotal Vs Infrapubic, International J. Impotence Res. (2003) 15, Suppl. 5, S134-S135.

Morey, Allen, et al, Immediate Insertion of a Semirigid Penile Prosthesis for Refractory Ischemic Priapism, Military Medicine, 172, 11:1211, 2007.

Mulcahy, John, Another Look At the Role of Penile Prostheses in the Management of Impotence, Urology Annual 11, pp. 169-185 (1997).

Natali, Alessandro, et al., Penile Implantation in Europe: Successes and Complications With W53 Implants in Italy and Germany, J Sex. Med. 2008;5:1503-12.

Paula, B. G. Revision Surgery for Penile Implants, Int. J. Impotence res. (1994) 6, 17-23.

Pearman RO. Insertion of a silastic penile prosthesis for the treatment of organic sexual impotence. J Urol. May 1972;107(5):802-6.

Randrup, Eduardo, Penile Implant Surgery: Rear Tip Extender That Stays Behind, Urology 1992 34, 1 pg 87.

Rhee, Eugene, Technique for Concomitant Implantation of the Penile Prosthesis With the Male Sling, J. Urol. 173: 925-927 (2006).

Salama, Nadar, Satisfaction With the Malleable Penile Prosthesis Among Couples From the Middle East: Is it Different From That Reported Elsewhere?, Int. J. Impotence Res. 16:175-180 (2004).

Simmons, M. et al., Penile Prosthesis Implantation: Past, Present and Future, Int. J. Impotence Res. (2008) 20, 437-44.

Small, Michael, Small-Carrion Penile Prosthesis: A Report on 160 Cases and Review of The Literature, J. Urol. vol. 167, 2357-2360, Jun. 2002.

Smith, Christopher, Management of Impending Penile Prosthesis Erosion With a Polytetrafluoroethylene Distal Wind Sock Graft, J. Urol. vol. 160: 2037-2040, (1998).

Stein, Avi et al., Malleable Penile Prosthesis Removal Leaving Behind The Rear TIP Extenders: A Clinical Presentation, Urol. Int. 50:119-120 (1993).

Surgical Protocol, Mentor 5 pages Sep. 1997.

The AMS Hydroflex Self-Contained Penile Prosthesis, American Medical Systems Publication 50513 (1985).

Yoo JJ, Lee I, Atala A. Cartilage rods as a potential material for penile reconstruction. J Urol. Sep. 1998;160(3 Pt 2):1164-8; discussion 1178.

Zerman, Dirk-Henrik, et al. Penile Prosthetic Surgery in Neurologically Impaired Patients: Long-Term Follow-Up, J Urol 175: 1041-1044. (2006).

* cited by examiner

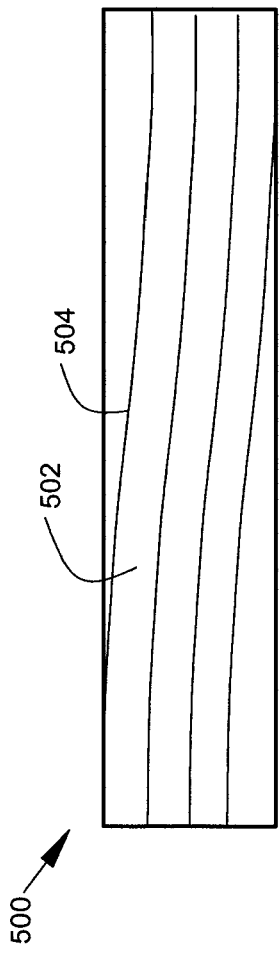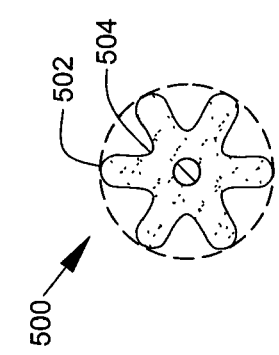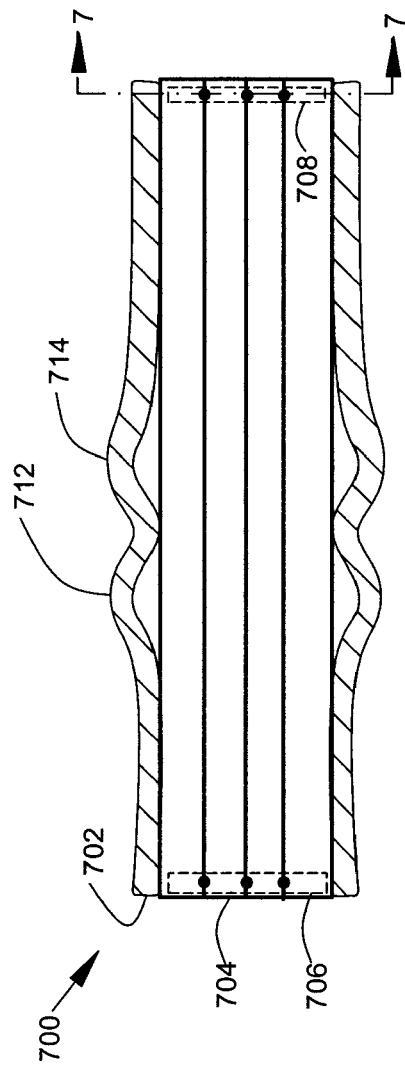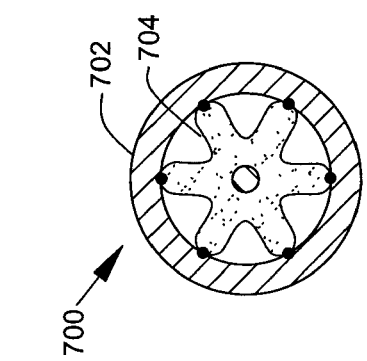

PROSTHETIC DEVICE WITH PROTRUSIONS FOR GIRTH

CLAIM TO PRIORITY

The present application claims priority to U.S. Provisional Patent Application No. 60/989,373, filed Nov. 20, 2007, and entitled "Prosthetic Device with Protrusions for Girth." The identified provisional patent application is hereby incorporated by reference in its entirety.

FIELD OF THE INVENTION

The present invention relates to implantable prostheses. In particular, but not by way of limitation, the present invention relates to implantable malleable (non-inflatable) penile prostheses.

SUMMARY OF THE INVENTION

Disclosed is a prosthetic device. The prosthetic device comprises a column formed of resilient material. The column comprises external protrusions that vary a girth of the column. The protrusions are separated by valleys that reduce bulk. In one embodiment, the prosthetic device further comprises a malleable core arranged inside the column.

BRIEF DESCRIPTION OF THE DRAWINGS

FIGS. 5-6 illustrate a third embodiment of a prosthesis.
FIGS. 7-8 illustrate a fourth embodiment of a prosthesis.

DETAILED DESCRIPTION OF ILLUSTRATIVE EMBODIMENTS

Figure 1:
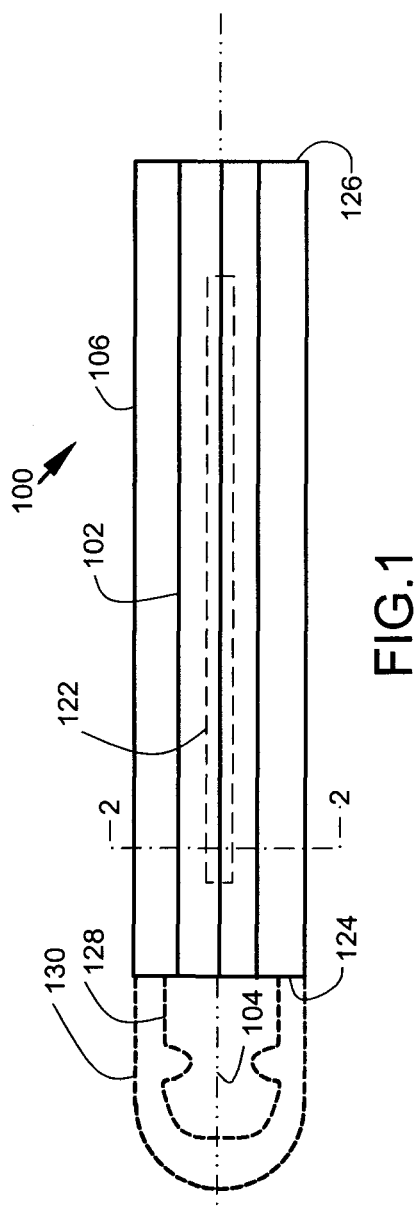
FIGS. 1-2 illustrate a first embodiment of a prosthesis.
Figure 2:
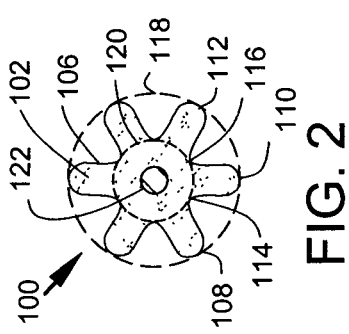

FIGS. 1-2 illustrate a penile prosthesis 100. FIG. 1 illustrates a side view of the prosthesis 100. FIG. 2 illustrates a cross-section view along line 2-2 in FIG. 1. The prosthesis 100 comprises a column 102 that comprises resilient material. The column 102 has an external surface 106 that is generally cylindrical and centered on a major axis 104 of the prosthesis 100. The external surface 106 comprises multiple lengthwise protrusions or flutes, such as representative flutes 108, 110, 112 that are separated by multiple lengthwise grooves, such as representative grooves 114, 116. The external surface 106 can be seen as fluted, channeled, grooved, ribbed or having lengthwise protrusions. In cross-section as illustrated in FIG. 2, the column 102 has a multi-petal or floret shape.

In one embodiment, the flutes 108, 110, 112 have protruding, large radius, broadly rounded distal surfaces that are free of sharp edges as illustrated. The large radius distal flute surfaces avoid stress concentrations in adjacent tissue that could otherwise injure adjacent tissue in contact with the flutes 108, 110, 112. Six flutes are illustrated in the example shown in FIGS. 1-2, however, it is understood that other numbers of flutes can also be used.

The flutes 108, 110, 112 extend outwardly to a major radius 118. The major radius 118 defines a girth of the prosthesis 100 that is expanded by the flutes 108, 110, 112. The grooves 114, 116 extend inwardly to a minor radius 120. The minor radius 120 defines an effective column radius for bending of the column 120. In terms of springback characteristics, the column 102 has springback characteristics that are enhanced by having the bending radius smaller than the girth. The term "springback" refers to the amount of a return movement of a bent column after a bending force is removed. Springback causes a column that is bent into a position (either a straight or bent position) to lose part of the bend after the column is released. Springback is an undesirable property that adversely affects concealability. Springback requires the user to learn to bend the column past a desired position in order for it to have the desired position after springback, or requires the user to bend the column multiple times in order to obtain a concealed position.

When the column 102 is bent, portions of the flutes 108, 110, 112 that are compressed can bow in a sideways direction to relieve compressive stress and reduce springback. Portions of the flutes 108, 110, 112 that are stretched upon bending exert a reduced springback force because the flutes have a narrowed cross-sectional area transverse to the longitudinal stretching direction.

In one embodiment, the prosthesis 100 comprises a malleable core 122. The malleable core can comprise a malleable core of known, conventional design. In one embodiment, the ends 124, 126 of the column 102 are flat as illustrated. In another embodiment, the ends 124, 126 of the column 102 are rounded or dome-shaped. In yet another embodiment the ends 124, 126 of the column 102 have snap fit protrusions, such as protrusion 128, which can receive snap-on end caps, such as cap 130, that have rounded or dome shapes.

Figure 3:
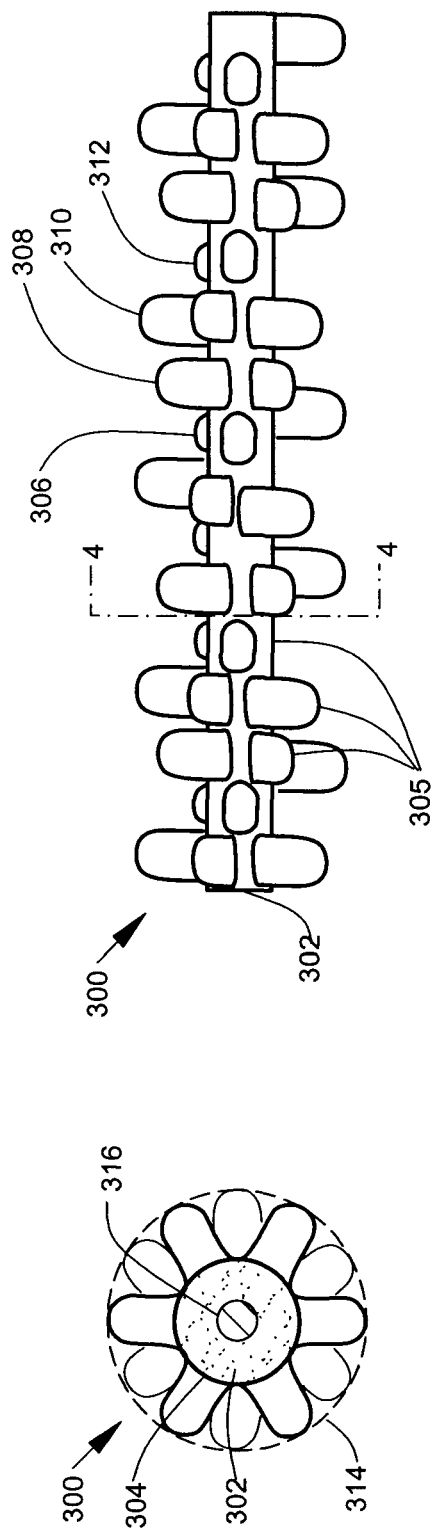
FIGS. 3-4 illustrate a second embodiment of a prosthesis.
Figure 4:
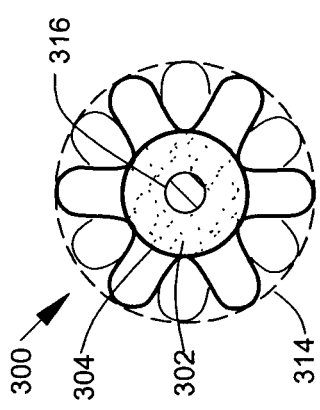

FIGS. 3-4 illustrate a penile prosthesis 300. FIG. 3 illustrates a side view of the prosthesis 300. FIG. 4 illustrates a cross-section view generally along line 4-4 in FIG. 3. The prosthesis 300 comprises a column 302 that comprises resilient material. The column 302 has an external surface 305 that generally comprises a cylindrical surface of minor radius 304 that is interrupted by multiple bumps or protrusions, such as representative protrusions 306, 308, 310, 312. The protrusions 306, 308, 310, 312 extend outwardly from the minor radius 304 to a major radius 314.

The protrusions 306, 308, 310, 312 are aligned in multiple radial directions at multiple lengthwise locations as illustrated. The protrusions 306, 308, 310, 312 are separated from one another by intervening valleys or open spaces as illustrated. The external surface 306 can be seen as knobby, bumpy or knurled. In cross-section as illustrated in FIG. 4, the column 302 has a petalled floret shape.

In one embodiment, the protrusions 306, 308, 310, 312 have large radius, broadly rounded distal surfaces that are free of sharp edges as illustrated. The large radius distal protrusion surfaces avoid stress concentrations in adjacent tissue that could otherwise injure adjacent tissue in contact with the protrusions 306, 308, 310, 312. The density or number of protrusions per unit area can vary from that shown, provided that there is a sufficient density of protrusions to provide a well defined major radius 314 and some separation space between protrusions. The major radius 314 defines a girth of the prosthesis 300 that is expanded by the protrusions 306, 308, 310, 312. The minor radius 304 defines an effective column radius for bending of the column 302. In terms of springback characteristics, the column 302 has springback characteristics that are enhanced by the having the bending radius smaller than the girth. The term "springback" refers to the amount of a return movement of a bent column after a bending force is removed. Springback causes a column that is bent into a position (either a straight or bent position) to lose part of the bend after the column is released. Springback is an undesirable property that adversely affects concealability. Springback requires the user to learn to bend the column past a desired position in order for it to have the desired position after springback, or requires the user to bend the column multiple times in order to obtain a concealed position.

When the column 302 is bent, the protrusions 306, 308, 310, 312 extend only a short distance along the column 302. The protrusions 306, 308, 310, 312, because of their short length, undergo little compression or tension during bending, and springback is reduced.

In one embodiment, the prosthesis 300 comprises a malleable core 316. The malleable core 316 can comprise a malleable core of known, conventional design. In one embodiment, the ends of the column 302 are flat as illustrated. In another embodiment, the ends of the column 302 are rounded or dome-shaped. In yet another embodiment the ends of the column 302 have snap fit protrusions which can receive snap-on end caps that have rounded or dome shapes.

FIGS. 5-6 illustrate a prosthetic device 500 that is similar to the prosthetic device 100 shown in FIGS. 1-2 except that flutes, such as representative flute 502, and grooves, such as representative groove 504, are not aligned straight but are twisted in a spiral pattern around a major longitudinal axis of the device 500. The spiral pattern provides an advantage in that it takes less force to bow the flutes sideways when the prosthetic device 500 is bent. In other respects the prosthetic device 500 is the same as the prosthetic device 100.

FIGS. 7-8 illustrate a prosthetic device 700 that is similar to the prosthetic device 100 shown in FIGS. 1-2 except that an external sheath 702 is applied around a column 704. FIG. 7 illustrates a cross sectional view along line 7-7 in FIG. 8. In other respects, the prosthetic device 700 is the same as the prosthetic device 100. An external sheath can also be applied to other columns such as columns 100, 300, 500.

The flexible sheath 702 surrounds a substantial portion of the length of the column 704 as illustrated. The flexible sheath 702 slides easily along the length of the column 704 so that bending the sheath does not build up any substantial internal stretching or compressive forces in the sheath 702 that could otherwise contribute to undesired springback. The flexible sheath, however, is attached to the ends of the column 704 in regions 706, 708 as indicated by solid dots where bonds are made. The flexible sheath 702 is provided with corrugations 712, 714 in a central region. The corrugations 712, 714 reduce axial tension and compressive forces in the sheath during bending, and reduce springback effects from the sheath 702. The sheath 702 can comprise materials such as silicone, urethane or polyurethane and other known flexible biocompatible materials. The sheath 702 tends to span across and cover up flutes and protrusions, giving the assembled prosthesis 700 a desired overall isodiametric shape, sensation and appearance. Sheaths 702 can be provided in different wall thickness to provide different girths adapted to individual patients, reducing inventory requirements for girth sizes of columns 700.

A semi-rigid column type of penile prosthesis offers the patient a device with good column strength and rigidity. The ability to conceal the device by positioning the column in a bent configuration and remaining in that concealed position can be challenging because of the large column diameter. The outside shape or profiles of the column shown in FIGS. 1-8 provide greater positionability and concealability. A malleable core can be used. Instead of having a smooth, isodiametric outside profile, profiles are provided that result in overall girth and allow the patient to have a column that remains in a desired, bent position for concealment. The floret-shaped cross-section for the column provides an overall large diameter along the column length and also less bulk to overcome along the column length in keeping the column in a desired, bent position (see attachment.) This outside shape gives the sensation and appearance of girth once implanted, because of the large diameter of distal ends in the floret pattern. Alternatively, a smaller diameter rod that has protrusions or bumps spaced along its length gives the outward appearance, once implanted in the corporal body, of a large girth and the sensation of fullness. It would also allow the bent column to remain in a desired position selected by a patient because of the minimal amount of material. The outside features could be molded directly on the rod or attached in a secondary operation.

Existing internal rod components (AMS 600, AMS 650, DURA II) and rear tip extenders (AMS 700 IPP or AMS Ambicor) could be used in these embodiments. An outside sheath could be used with each of the embodiments. The sheath can be installed in different wall thicknesses to provide different girths for different patients, and to reduce inventorying multiple column sizes. Internal core components from AMS 600, AMS 650, Dura II can be adapted for use in the rod. Existing snap attachment RTEs (AMS 700 IPP, AMS Ambicor) can be used as rod ends.

Although the present invention has been described with reference to preferred embodiments, workers skilled in the art will recognize that changes may be made in form and detail without departing from the spirit and scope of the invention.

What is claimed is:

1. A penile prosthetic device, comprising:
  a column formed of resilient material and having external protrusions that vary girth, wherein the protrusions are separated by valleys that reduce bulk and are presented in a floret configuration around a diameter of the column.

2. The prosthetic device of claim 1 and further comprising a malleable core arranged inside the column.

3. The prosthetic device of claim 2, wherein the protrusions are presented around a diameter and along a length of the column.

4. The prosthetic device of claim 2, further including a sheath about the column.

5. The prosthetic device of claim 4, wherein said sheath is removable.

6. The prosthetic device of claim 1, wherein the valleys define grooves that extend along a length of the column.

7. The prosthetic device of claim 6, wherein the grooves are twisted about a major axis of the column.

8. A penile prosthetic deice comprising:
  a column formed of resilient material having an external surface and a major axis;
  a plurality of protrusions around the column protruding in a radial direction relative to the major axis, wherein the plurality of protrusions displaced from each other along the major axis; and
  a sheath covering the column and the plurality of protrusions, wherein the sheath comprises corrugations extending around the column.

9. The device of claim 8, further comprising a malleable core arranged inside the column.

10. The device of claim 9, wherein the malleable core has a generally cylindrical external surface.

11. The device of claim 8, wherein the protrusions are arranged in a floret configuration around a diameter of the column.

12. A penile prosthetic device comprising:
   a column formed of resilient material having an external surface and a major axis;
   a plurality of protrusions around the column protruding in a radial direction relative to the major axis, wherein the plurality of protrusions define grooves between adjacent protrusions that extend parallel to the major axis.

13. The device of claim 12, further comprising a cylindrical malleable core arranged inside the column.

14. The device of claim 13, wherein the malleable core is coaxial with the major axis.

15. The device of claim 12, further comprising a sheath covering the column and the plurality of protrusions.

16. The device of claim 15, wherein the sheath comprises corrugations extending around the column.

* * * * *